US012806122B2

(12) United States Patent
Wei et al.

(10) Patent No.: US 12,806,122 B2
(45) Date of Patent: Nov. 24, 2026

(54) NUTRIENT INFUSION APPARATUS AND CONTROL METHOD THEREFOR

(71) Applicant: Medcaptain Medical Technology Co., Ltd., Shenzhen (CN)

(72) Inventors: Liyan Wei, Shenzhen (CN); Xiaocheng Tang, Shenzhen (CN)

(73) Assignee: Medcaptain Medical Technology Co., Ltd., Shenzhen (CN)

( * ) Notice: Subject to any disclaimer, the term of this patent is extended or adjusted under 35 U.S.C. 154(b) by 0 days.

(21) Appl. No.: 18/928,023

(22) Filed: Oct. 26, 2024

(65) Prior Publication Data

US 2025/0134776 A1 May 1, 2025

(51) Int. Cl.

*A61J 15/00* (2006.01)
*A61M 1/36* (2006.01)
*G16H 20/17* (2018.01)
*A61M 5/14* (2006.01)
*A61M 5/142* (2006.01)

(52) U.S. Cl.

CPC ....... *A61J 15/0076* (2015.05); *A61J 15/0026* (2013.01); *A61J 15/0088* (2015.05); *A61M 1/3643* (2013.01); *A61M 1/3646* (2014.02); *G16H 20/17* (2018.01);

(Continued)

(58) Field of Classification Search

CPC .... A61J 15/0076; A61J 15/00; A61J 15/0084; A61J 15/0088; A61J 15/0092; A61M 5/16827; A61M 2005/14208; A61M 5/142; A61M 5/14228; A61M 5/172; A61M 39/281; A61M 5/14216; A61M 2205/3334; A61M 5/16804; A61M 2205/14; A61M 5/1684; E03D 1/00; G16H 20/17

See application file for complete search history.

(56) References Cited

U.S. PATENT DOCUMENTS

2008/0119822 A1* 5/2008 Knauper ............. A61J 15/0076
604/151
2020/0000682 A1* 1/2020 Hoffstetter .......... A61J 15/0076

FOREIGN PATENT DOCUMENTS

CN 106659835 A * 5/2017 .......... A61M 1/1621
CN 108096035 A * 6/2018 .......... A61J 15/0076

(Continued)

OTHER PUBLICATIONS

CN 113367992 A, English language machine translation (Year: 2021).*

(Continued)

*Primary Examiner* — Wesley G Harris
(74) *Attorney, Agent, or Firm* — Jeffrey Pearce

(57) ABSTRACT

A method for controlling a nutrient infusion apparatus, includes: acquiring a feeding parameter; automatically determining a first flushing parameter according to the feeding parameter and a preset flushing rule; and controlling the nutrient infusion apparatus to flush according to the first flushing parameter. Healthcare personnel, when setting parameters, thus only need to set the feeding parameter, and the corresponding flushing parameter can be determined automatically. Furthermore, relative to having to set the flushing parameter manually, the accuracy of automatically determining the flushing parameter according to the feeding parameter is also higher, which improves the accuracy of parameter setting, which in turn improves the accuracy of the flushing control.

11 Claims, 7 Drawing Sheets

(52) U.S. Cl.
CPC ............... *A61M 2005/1403* (2013.01); *A61M 2005/14208* (2013.01); *A61M 2205/33* (2013.01); *A61M 2205/3334* (2013.01)

(56) References Cited

FOREIGN PATENT DOCUMENTS

| | | | | |
|---|---|---|---|---|
| CN | 113367992 | A | * | 9/2021 |
| CN | 216496555 | U | * | 5/2022 |
| CN | 115040416 | A | * | 9/2022 |

OTHER PUBLICATIONS

CN 216496555 U, English language machine translation (Year: 2022).*
CN 106659835 A, English language machine translation (Year: 2017).*
CN 108096035 A English language machine translation (Year: 2018).*
CN 115040416 A English language machine translation (Year: 2022).*

* cited by examiner

NUTRIENT INFUSION APPARATUS AND CONTROL METHOD THEREFOR

REFERENCE TO RELATED APPLICATIONS

The invention claims priority of Chinese Patent Application No. 202311409802.3, entitled "Nutrient Infusion Apparatus and Control Method Therefor" filed with the China National Intellectual Property Administration on October. 26, 2023, which is incorporated herein by reference in its entirety.

TECHNICAL FIELD

This invention generally relates to medical apparatus, and more particularly, to a nutrient infusion apparatus and a control method therefor.

BACKGROUND ART

During the process of enteral nutrition infusion, complications such as tube blockage and diarrhea are common. Flushing the tube can effectively prevent nasal feeding tube blockage and also help with hydration. However, excessive flushing within a short period may also lead to the occurrence of the complication diarrhea.

In the prior art, a nutrition infusion apparatus with automatic flushing functions can automatically flush the tube during the feeding process after determining the flushing parameters. This reduces the need for manual operations by medical staff while still achieving the tube-flushing effect.

However, the flushing parameters of existing nutrient infusion apparatus can only be set manually by the healthcare professional, and the efficiency of parameter setting is low. Moreover, it is not possible to adjust the flushing program according to the working status of the nutrient infusion apparatus during the actual feeding process, and there will still be a blockage of the tube or an excessive amount of flushing, which degrades the therapeutic effect.

Moreover, currently available nutrient infusion device require medical staff to set the flushing parameters manually, which results in low efficiency. Additionally, they cannot adjust the flushing program according to a working state of the nutrient infusion apparatus during the actual feeding process. This may still lead to tube blockage or excessive flushing, thus affecting the overall treatment effectiveness.

SUMMARY OF THE INVENTION

The invention provides a nutrient infusion apparatus and a control method therefor that aims to solve the problem of improving the efficiency of parameter setting and preventing feeding tube blockage and excessive flushing.

In a first aspect, the invention provides a method for controlling a nutrient infusion apparatus, comprising:

- acquiring a feeding parameter;
- automatically determining a first flushing parameter according to the feeding parameter and a preset flushing rule; and
- controlling the nutrient infusion apparatus to flush a feeding tube according to the first flushing parameter.

In an embodiment, the feeding parameter comprises at least one of the following: a nutrient solution type, a nutrient solution concentration, a nutrient solution feeding volume, a feeding mode, a feeding rate, a feeding time, and a patient type.

In an embodiment, the first flushing parameter comprises at least one of the following:

- a flushing mode, a flushing rate, a total flushing volume, a flushing time, a flushing volume per cycle, and a number of flushing cycles.

In an embodiment, after the step of determining the first flushing parameter according to the feeding parameter and preset flushing rule, the method further comprises:

- acquiring working state information of the nutrient infusion apparatus; and
- adjusting the first flushing parameter according to the working state information and a preset parameter adjustment strategy.

In an embodiment, the working state information comprises at least one of the following: feeding pause duration, manual flushing information, and tube blockage information; wherein the tube blockage information comprises at least one of a tube blockage frequency and a tube blockage pressure value.

In an embodiment, the step of adjusting the first flushing parameter according to the working state information and a preset parameter adjustment strategy comprises adjusting the first flushing parameter according to the working state information when it is determined that the working state information satisfies a preset parameter adjustment condition.

In an embodiment, the method further comprises:

- displaying a flushing parameter adjustment interface;
- receiving input from a user in the flushing parameter adjustment interface and thereby obtaining a second flushing parameter input by the user; and
- adjusting the first flushing parameter according to the second flushing parameter entered by the user.

In an embodiment, the method further comprises outputting a prompt message when it is determined that the second flushing parameter input by the user exceeds a preset threshold.

In a second aspect, the invention provides a nutrient infusion apparatus, comprising:

- an acquisition unit configured to acquire a feeding parameter;
- a parameter determination unit configured to determine a first flushing parameter according to the feeding parameter and a preset flushing rule; and
- a control unit configured to control the nutrient infusion apparatus to flush according to the first flushing parameter.

In a third aspect, the invention provides a nutrient infusion apparatus that comprises: a processor, and a memory in communication with the processor;

- wherein the memory is configured to store computer-executable instructions; and the processor is configured to execute the computer-executable instructions stored in the memory to implement the method as previously described.

In a fourth aspect, the invention provides a computer-readable storage medium having computer-executable instructions stored thereon, wherein the computer-executable instructions, when executed, perform the method as previously described when executed by the processor.

In a fifth aspect, the invention provides a computer program product comprising a computer program, the computer program, when executed by a processor, being configured to implement a method as previously described.

The invention provides a nutrient infusion apparatus and a control method therefor, including: acquiring a feeding parameter; automatically determining a first flushing parameter according to the feeding parameter and a preset flushing rule; and controlling the nutrient infusion apparatus to flush according to the first flushing parameter. Using the method of the invention, healthcare personnel, when performing parameter setting, only need to set the feeding parameter, and the corresponding flushing parameter can be determined automatically, without also having to set the flushing parameter manually, thereby improving the efficiency of parameter setting. Furthermore, relative to manually setting the flushing parameter, the accuracy achieved by automatically determining the flushing parameter according to the feeding parameter is also higher, which also improves the accuracy of parameter setting, thereby improving the accuracy of the flushing control.

BRIEF DESCRIPTION OF THE DRAWINGS

The accompanying drawings herein, which are incorporated into and form a part of the specification, illustrate embodiments consistent with the invention and are used in conjunction with the specification to explain the principles of the invention.

Figure 1A:
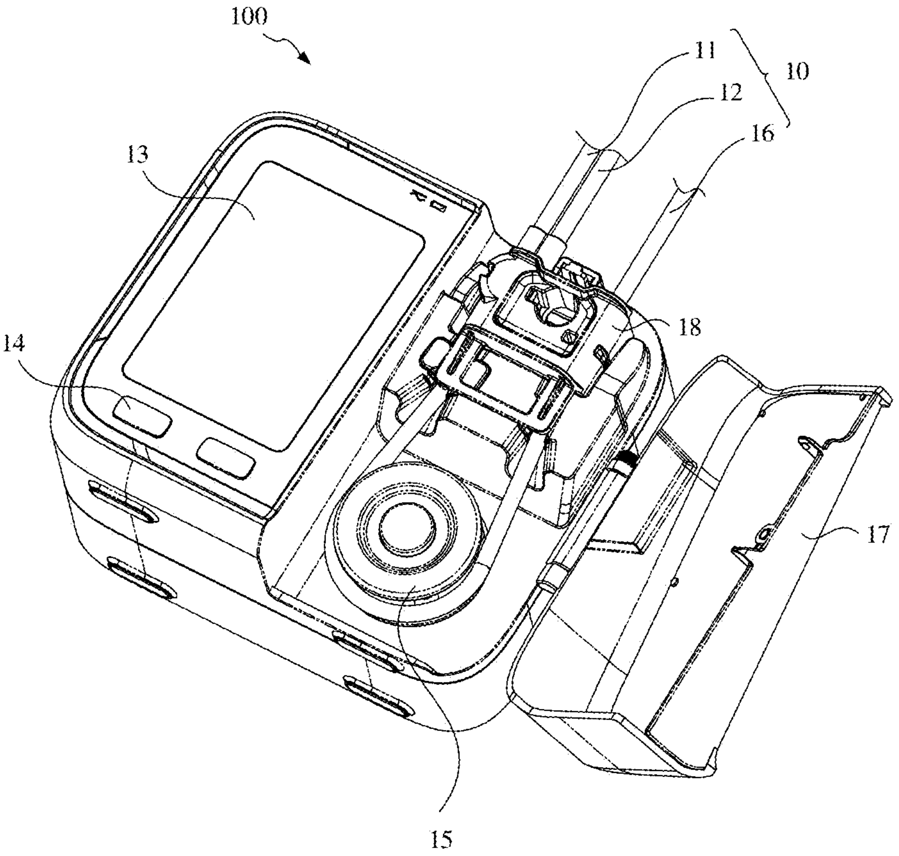
FIG. 1A shows a schematic structural diagram of a nutrient infusion apparatus according to an embodiment of the invention.

By means of the above accompanying drawings, definite embodiments of the invention are shown, and will be described in more detail later. These accompanying drawings and textual descriptions are not intended to limit the scope of the invention in any way, but rather to illustrate the concepts of the invention for those skilled in the art by reference to particular embodiments.

DETAILED DESCRIPTION

Example embodiments will be described herein in detail, which are represented in the accompanying drawings. When the following description relates to the accompanying drawings, the same numerals in the different accompanying drawings indicate the same or similar elements unless otherwise indicated. The embodiments described in the following example embodiments do not represent all embodiments consistent with the invention. Rather, they are only examples of devices and methods consistent with some aspects of the invention as defined in the appended claims.

The terms "first", "second", "third", "fourth" and the like, if any, in the specification and claims of the invention and the accompanying drawings described above are used to distinguish similar objects and need not be used to describe a particular order or sequence. It should be understood that the number used in the specification may be interchanged, where appropriate, so that the embodiments of the invention described herein may be practiced in an order other than those illustrated or described herein. In addition, the terms "include" and "have", and any variations thereof, are intended to cover non-exclusive inclusion, for example, a process, method, system, product or apparatus including a series of steps or units need not be limited to those clearly listed, but may include other steps or units that are not clearly listed or that are inherent to the process, method, product or apparatus.

Tube flushing is routinely performed during enteral nutrition infusion to prevent tube blockage while also rehydrating a patient. Such tube flushing can effectively prevent blockage of the nasoenteric tube, but excessive tube flushing within a short period of time may also lead to diarrhea complications. Therefore, it is necessary to accurately control the flushing parameters to ensure therapeutic efficacy.

Currently available nutrient infusion apparatuses require medical staff to manually set the flushing parameters, which results in low efficiency. Additionally, they cannot adjust the flushing program according to a working state of the nutrient infusion apparatus during the actual feeding process. This may still lead to tube blockage or excessive flushing, thus affecting the overall treatment effectiveness.

In order to solve the above problems, the invention provides a method for controlling a nutrient infusion apparatus, in which the invention takes into account that the flushing of the nutrient infusion apparatus is closely related to the feeding process, and therefore associates the feeding parameters with the flushing parameters, so that after the user has set the feeding parameters, the flushing parameters are determined directly and automatically according to preset flushing rules, without staff having to manually set the flushing parameters. This improves the efficiency of parameter setting. In addition, the invention also obtains information on the working status of the nutrient infusion apparatus during the actual feeding process, so as to adjust the flushing parameters according to the actual feeding situation, thereby reducing the risk of tube blockage and avoiding excessive flushing in a short period of time; this improves the therapeutic effect.

In order to solve the aforementioned problems, the invention provides a method for controlling the nutrient infusion apparatus. Considering the close relationship between the flushing process and the feeding process of the nutrient infusion apparatus, the feeding parameters are linked with the flushing parameters. After the user sets the feeding parameters, the flushing parameters are automatically determined based on preset flushing rules without needing manual input, thereby improving parameter-setting efficiency. Additionally, during the actual feeding process, the working state information of the nutrient infusion apparatus is acquired and is used to adjust the flushing parameters according to the real-time feeding conditions. This reduces the risk of tube blockage and prevents excessive flushing within a short period, ultimately improving the treatment effectiveness.

The technical solution of the invention and how it solves the above technical problems are described in detail below by means of specific embodiments. The following specific embodiments may be combined with each other, and the same or similar concepts or processes need not be duplicated in certain embodiments. Embodiments of the invention will be described below in conjunction with the accompanying drawings.

Firstly, the structure of the nutrient infusion apparatus involved in the invention is a briefly introduced.

Figure 1B:
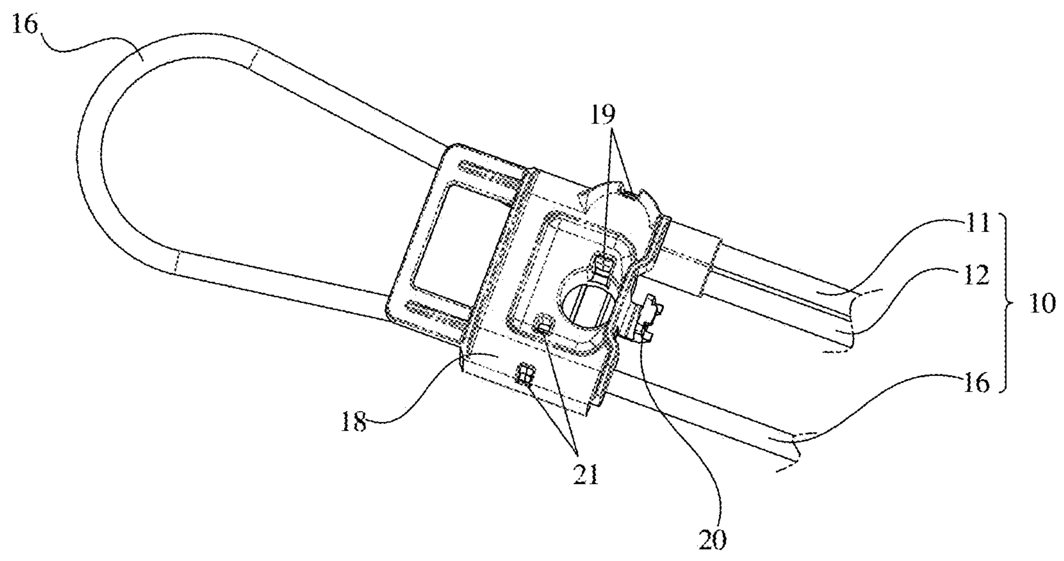
FIG. 1B shows a schematic structural diagram of an infusion tube according to an embodiment of the invention.

As an example, FIG. 1A shows a schematic structural diagram of a nutrient infusion apparatus according to an embodiment of the invention; FIG. 1B, similarly, shows a schematic structural diagram of an infusion tube according to an embodiment of the invention. The structural diagram of the infusion tube shown in FIG. 1B is a detailed illustration of a a portion of the infusion tube in the nutrient infusion apparatus shown in FIG. 1A. As shown in FIG. 1A and FIG. 1B, the nutrient infusion apparatus 100 of the invention includes at least a controller (not shown in the figures), a driving member (not shown in the figures), an actuating member 15, and delivery tubing 10. The controller is electrically connected to the driving member, and the driving member is connected to the actuating member for power transmission, and the actuating member is disposed in a tubing path of the delivery tubing 10. The driving member, under the control of the controller, drives the actuating member 15 to rotate so as to drive the fluid flow in the delivery tubing 10. The delivery tubing 10 includes a nutrient fluid tube 11, a flushing fluid tube 12, and a silicone tube 16. When the nutrient infusion apparatus 100 performs infusion, the conduction of the nutrient fluid tube 11 and the flushing fluid tube 12 is controlled by a three-way valve (not shown in the figures), so as to control the nutrient infusion apparatus 100 to infuse nutrient fluid or flushing fluid.

In addition, as shown in FIG. 1A, the nutrient infusion apparatus 100 may also include components such as a display screen 13, buttons 14, a pump door 17, and a consumable support plate 18. As shown in FIG. 1B, the three-way valve may be secured by means of a snap slot 19; the consumable support plate 18 may be secured by means of the consumable support plate snap 20; and the tubing 10 may be secured by means of a snap slot 21 provided on a tubing connector. The display screen 13 is configured to display parameter information related to nutrient infusion, so that the healthcare professional may set the feeding parameters, flushing parameters, and other information displayed on the display screen.

Next, the process of how to control the nutrient infusion apparatus for feeding and flushing is described in detail.

Figure 2:
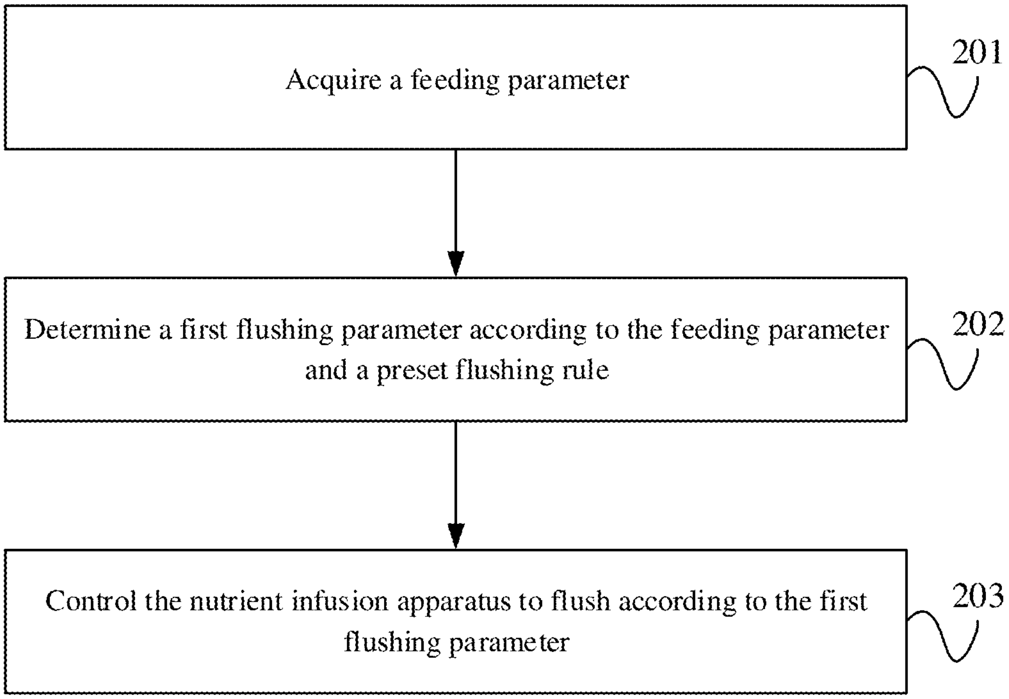
FIG. 2 shows a flowchart of a method for controlling the nutrient infusion apparatus according to an embodiment of the invention.

FIG. 2 shows a flowchart of a method for controlling a nutrient infusion apparatus provided by an embodiment of the invention. The method of the embodiments of the invention may be carried out by a control device of the nutrient infusion apparatus. The control device may be disposed on the nutrient infusion apparatus, or may be disposed on a medical device such as an infusion central station, an infusion workstation, an infusion monitoring system, or the like, which is connected to the nutrient infusion apparatus; the invention is not limited to this arrangement. The embodiments of the invention are described in detail using the subject as the control device as an example.

As shown in FIG. 2, the embodiment provides a method for controlling a nutrient infusion apparatus, including the following steps.

S201, feeding parameters are acquired.

As an example, when the nutrient infusion apparatus shown in FIG. 1A is powered on, a setting interface for the feeding parameters may be shown in the display screen, and a user may set the feeding parameters according to the setting interface to enable the control device of the nutrient infusion apparatus of the invention to acquire the feeding parameters. In addition, the control device may also acquire the feeding parameters from other devices such as a medical system, the cloud, an infusion central station, an infusion workstation, or an infusion monitoring system, etc.

The feeding parameters characterize parameters related to the nutrient solution feeding process. For example, the feeding parameters may include at least one of the following: a nutrient solution type, a nutrient solution concentration, a nutrient solution feeding volume, a feeding mode, a feeding rate, a feeding time, a patient type, etc.

As an example, the healthcare personnel may, according to the actual nutrient infusion needs of the feeding subject, sequentially set the nutrient solution type, the nutrient solution concentration, the nutrient solution feeding volume, the feeding mode, the feeding rate, the feeding time, and the patient type of the nutrient solution to be infused into the feeding subject on the setting interface of the feeding parameter. The feeding mode may be continuous feeding or intermittent feeding.

As an example, in the continuous feeding mode, feeding is generally a continuous over a period of more than 24 h. Continuous feeding is better tolerated by patients with poor intestinal absorption ability or gastrointestinal dysfunction, and it is also a feeding mode that is more widely used in patients with severe clinical conditions. Intermittent feeding generally refers to a feeding mode that provides 4-6 feedings per day, each lasting 20-60 minutes, which is more in line with physiological characteristics, and facilitates the feeding subject to get out of bed or carry out activities such as treatment and examination. When setting the parameters, healthcare personnel can choose the appropriate feeding mode according to the physical condition of the feeding subject. that is, patient, and the treatment plan to be carried out. For example, if the feeding subject is a critically ill patient with poor intestinal absorption, continuous feeding may be selected to provide sufficient nutrition for the feeding subject. If the feeding subject needs to do supplementary training or needs to be examined at a specific time period, intermittent feeding may be selected to facilitate scheduling of the feeding subject.

In one possible example, the feeding parameters may also be indirectly determined by analyzing the nutrient infusion requirement information of the feeding subject and/or the feeding subject information and/or vital sign state parameters. The nutrient infusion requirement information may include at least one of the following: the nutrient solution type, the feeding mode, the feeding rate, the feeding volume, and the feeding time. The feeding subject information may include at least one of the following: a patient's body weight, body weight change, age, calorie consumption, height, gender, a patient type, and disease information. The vital sign state parameters may include at least one of an end-tidal carbon dioxide indication EtCO2, a hemodynamic indication, a blood glucose indication, a heart rate, a blood pressure, an electrocardiogram, a body temperature, an oxygen saturation, and a pulse. For example, instead of entering the feeding parameters themselves, the healthcare personnel may enter information about the nutrient infusion requirements of the feeding subject and/or the feeding subject information and/or the vital sign state parameters in the setting screen for the feeding parameter. This information may be obtained from any chosen source, such as, for example, the patient monitor, a Hospital Information System (HIS), a Clinical Information System (CIS), etc. The nutrient infusion apparatus may automatically analyze these parameters after acquiring them to determine the feeding parameters of the invention.

The invention does not impose restrictions on how the nutrient infusion apparatus determines the feeding parameters according to the nutrient infusion requirement information of the feeding subject and/or the feeding subject information and/or the vital sign state parameters. For example, the nutrient infusion demand information of the feeding subject and/or the feeding subject information and/or the vital sign state parameters may be input into a predetermined data analysis model, a neural network model, a clustering model, or the like, to determine that the parameters outputted by the model are the feeding parameters. Alternatively, the historical feeding parameters of the feeding subject may be retrieved, and then the nutrient infusion requirement information and/or the feeding subject information and/or the vital sign state parameters of the feeding subject may be compared and matched with the historical feeding parameters, and the historical feeding parameter with the highest match is determined to be the current feeding parameter. The nutrient infusion requirement information of the feeding subject and/or the feeding subject information and/or the vital signs state parameters may be analyzed in various ways, so that the feeding parameters can be determined.

S202, according to the feeding parameters and the preset flushing rule, the first flushing parameters are determined.

As an example, after acquiring the feeding parameters, the control device of the nutrient infusion apparatus of the invention can automatically generate a set of suitable flushing schemes according to the feeding parameters and the preset flushing rule, which has a corresponding first flushing parameter and which is a flushing default value. The healthcare personnel then only need to set the feeding parameters and do not need to set the flushing parameters. This improves the efficiency of parameter setting.

As an example, the flushing parameter characterizes the parameters associated with the flushing process. For example, the flushing parameter may include at least one of the following: a flushing mode, a flushing rate, a total flushing volume, a flushing time, a flushing volume per cycle, and a number of flushing cycles. The flushing mode may be pulsed flushing or steady flushing, which may, but need not, have a different flushing rate than for pulsed flushing.

As an example, pulsed flushing may be a flushing mode that uses push-and-stop flushing, which can make the flushing liquid generate positive and negative pressure so as to form a vortex in the cavity of the flushing tube. This then increases the thorough and uniform flushing of the tube (such as a catheter) wall, powerfully flushing the residual drug attached to the catheter wall, and reducing the occurrence of blockage more effectively. Uniform flushing is a flushing mode that provides a continuous, uniform flow of flushing fluid. The closer to the center axis of the tube, the greater the flow rate will be, and the closer to the wall, the smaller the flow rate will be. The flow rate along the tube wall will be close to zero, and the flushing effect will be limited. In determining the flushing mode, if the nutrient solution is viscous, and/or the nutrient solution concentration is larger, in order to achieve a better flushing effect and effectively avoid blocking the tube, the device may be set to the pulsed flushing mode. If it is determined that the feeding subject does not have a high demand for the flushing effect, and it is necessary to replenish water, the device may preferably be set to the uniform flushing mode.

In one embodiment, the preset flushing rule may be determined according to a correspondence between the feeding parameters and the flushing parameters, and the flushing parameters used for different feeding parameters may be different. Other flushing rules may instead be chosen, however. For example, when determining the flushing parameters, the flushing mode and the flushing rate may be set according to the nutrient solution type and/or the nutrient solution concentration. The flushing time and the flushing volume per cycle are determined according to the flushing total volume and the feeding mode. The flushing parameters corresponding to the feeding parameters of the different feeding subjects may be different, which should be considered in conjunction with the overall situation of the feeding subject. For example, when the nutrient solution with a nutrient solution type in the feeding parameters is relatively more viscous, and/or the nutrient solution concentration is large, then according to the preset flushing rule, a larger flushing rate, a larger total flushing volume, shorter flushing times, and a larger number of flushing cycles may be set. On the other hand, if nutrient solution with a nutrient solution type in the feeding parameters is dilute and/or the nutrient solution concentration is small, then, according to the preset flushing rule, a smaller flushing rate, a smaller total flushing volume, a smaller amount of flushing may be set. Of course, based on the preset flushing rule, corresponding flushing parameters may also be determined according to at least one of other feeding parameters (e.g., nutrient solution feeding volume, feeding mode, feeding rate, feeding time, patient type), etc.

For example, a mapping table characterizing the correspondence between each feeding parameter and each flushing parameter may be experimentally or computationally established. For example, the mapping table may include the correspondence between the nutrient solution type and the flushing mode, the correspondence between the nutrient solution concentration and the flushing rate, the correspondence between the feeding mode and the flushing time, and so on. When the nutrient solution type is chosen, the flushing mode may then be selected according to the correspondence between the nutrient solution type and the flushing mode in the mapping table. When the nutrient solution concentration is known, the flushing rate may also be set according to the correspondence between the nutrient solution concentration and the flushing rate in the mapping table, and so forth. Each parameter of the flushing parameter may thus be determined according to the information in the mapping table.

In addition, in another embodiment, the preset flushing rule may be chosen according to a formula that represents a functional relationship between one or more feeding parameters and each flushing parameter, in which the input parameter is one or more feeding parameters and the output function value is a flushing parameter. A plurality of formulas may be determined experimentally and/or theoretically and included in the preset flushing rule, with the output function value of each formula corresponding to a different flushing parameter. When one or more feeding parameters are obtained, they may then be substituted as parameters in the chosen formula and the corresponding flushing parameters can be calculated. Alternatively, the corresponding feeding parameters may also be calculated “inversely” according to the flushing parameters and the respective formula. functional relationship equation. For example, given the nutrient solution feeding volume and the feeding rate, the feeding time, that is, the duration of the feeding, can be calculated. When the feeding time exceeds a preset threshold, a flush cycle may be performed periodically, for example, once for every n hours of continuous feeding. Accordingly, given the feeding time and the number n, the number of flushing cycles can be calculated. For example, if the flushing rate should be m times the feeding rate, then after determining the feeding rate, it will be possible to calculate the flushing rate. For the feeding parameter and the flushing parameter, which have a functional relationship, the corresponding parameter values can be determined in this manner.

Further, in yet another embodiment, the preset flushing rule may also be a combination of the above mapping table and the respective formula. For example, when the user sets the nutrient solution type to be infused into the feeding subject on the parameter setting interface, then, given the correspondence between the nutrient solution type and the flushing mode in the mapping table, the proper flushing mode can be determined. When the nutrient solution concentration is set, according to the correspondence between the nutrient solution concentration and the flushing rate in the mapping table, the flushing rate can be determined, and so forth. Thus, the flushing parameters calculated by the respective formula can also be determined. Accordingly, a flushing parameter matching the feeding parameter may be determined by correspondence and the functional relationship existing between the parameters.

In still another embodiment, the preset flushing rule may also be a correspondence between the input of the feeding parameters and the output of the flushing parameters established by a data analysis model, a machine learning algorithm, a neural network algorithm, a clustering algorithm, an expert system, or the like. Thus, a more accurate flushing parameter can be determined according to the acquired feeding parameters and the above preset flushing rule. As an example, the predetermined data analysis model may be pre-trained on at least one of the feeding parameters and configured to determine the flushing parameters according to the at least one of the feeding parameters. After inputting at least one of the feeding parameters into the predetermined data analysis model, the predetermined data analysis model may perform the data analysis to output a recommended flushing strategy, and the flushing strategy output by the predetermined data analysis model may be used as a flushing parameter in this invention.

In one possible example, after determining the first flushing parameter according to the feeding parameters and the preset flushing rule, the user may also adjust the first flushing parameter to make the first flushing parameter more consistent with the flushing demand, thereby improving the flushing effect. Therefore, the control method of the invention may also include the following steps.

S10, a flushing parameter adjustment interface is displayed.

S20, an input from the user in the flushing parameter adjustment interface is received, and the second flushing parameter input by the user is determined.

S30, the first flushing parameter is adjusted according to the second flushing parameter input by the user.

As an example, after determining the first flushing parameter, the flushing parameter adjustment interface may also be controlled to be displayed in a display of the nutrient infusion apparatus, and the user may adjust the flushing parameter on the flushing parameter adjustment interface. In an embodiment, a second flushing parameter input by the user at the flushing parameter adjustment interface is received, so as to adjust the first flushing parameter according to the second flushing parameter. The second flushing parameter may be an adjustment value or a target value. When the second flushing parameter is an adjustment value, the first flushing parameter is adjusted with the adjustment value indicated by the second flushing parameter to obtain a new flushing parameter. When the second flushing parameter is a target value, the value indicated by the second flushing parameter is set to be the new flushing parameter. The adjusted flushing parameter may be more in line with the flushing needs of the healthcare personnel, and flushing the tube with the adjusted flushing parameter can have a better flushing effect, thereby improving the treatment effectiveness.

Figure 3:
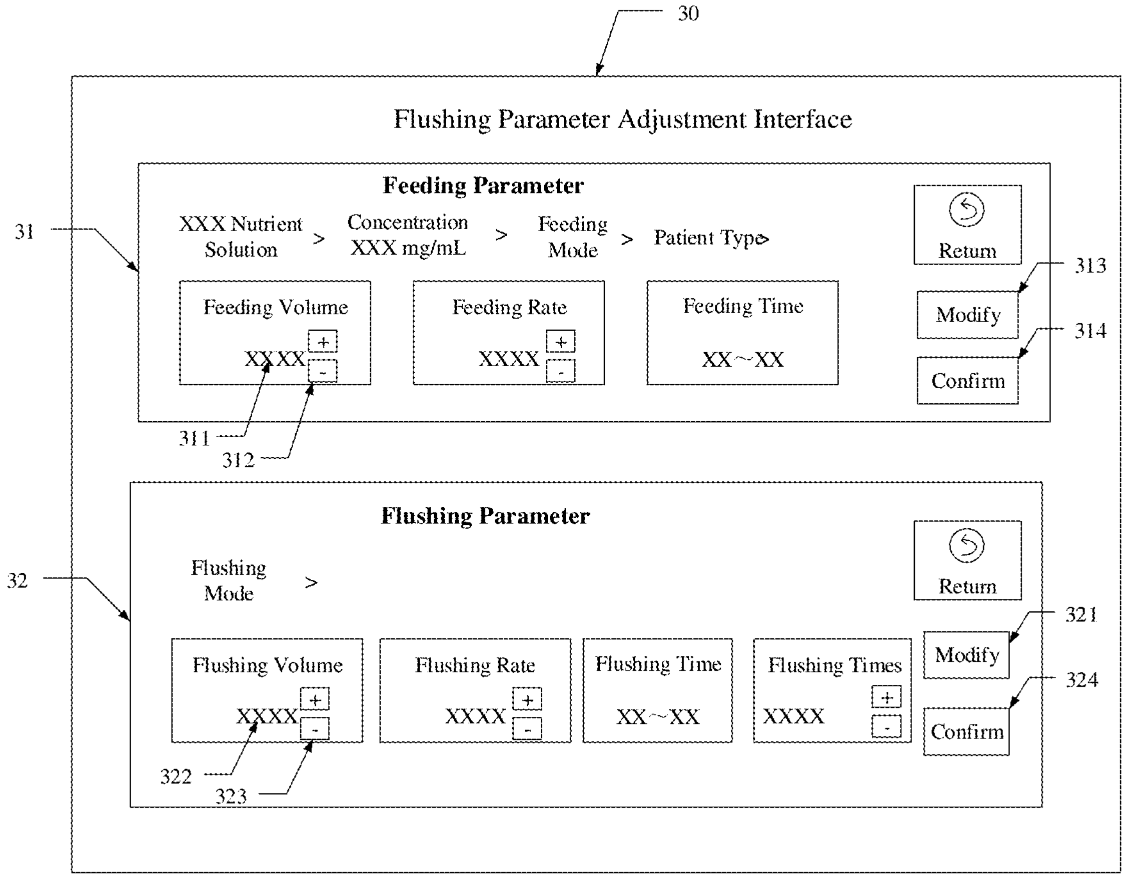
FIG. 3 is a schematic diagram of a flushing parameter adjustment interface according to an embodiment of the invention.

As an example, FIG. 3 shows a schematic diagram of a flushing parameter adjustment interface provided by an embodiment of the invention. As shown in FIG. 3, a feeding parameter setting window 31 and a flushing parameter adjustment window 32 may be displayed in the flushing parameter adjustment interface 30. The feeding parameter information such as the nutrient solution type, the nutrient solution concentration, the nutrient solution feeding volume, the feeding mode, the feeding rate, the feeding time, the patient type, etc., is displayed in the feeding parameter setting window 31. When setting the feeding parameters, the user can directly click on the parameter itself, such as "XXXX" 311 to enter the corresponding parameter setting value. If the parameter setting value is to be adjusted after setting the parameter, it can be adjusted by clicking on the "+"/"−" control 312 to increase/decrease the corresponding value, or click on the 'Modify' control 313 of the feeding parameter to change the value; this is just one possible configuration. After the user sets the feeding parameters, the flushing parameters displayed in the flushing parameter adjustment window 32 will be automatically generated, and if the user wants to adjust the flushing parameters, the user can directly click on the "Modify" control 321 of the flushing parameters in the interface to modify the flushing parameters, or can directly click on the parameter itself "XXXX to input the corresponding value of the parameter to be adjusted, or click on the "+"/"−" control 323 to increase/decrease the corresponding value, or perform some other predetermined action on the display screen.

In some examples, the feeding parameter setting window 31 and the flushing parameter adjustment window 32 in the flushing parameter adjustment interface 40 shown in FIG. 3 may also display a feeding parameter "Confirm" control 314 and a flushing parameter "Confirm" control 324. When the user determines the feeding parameters via the "Confirm" control 314, the feeding parameters take effect, and the flushing parameter is automatically determined according to the preset flushing rule of the invention. When the user sets the first flushing parameters via the "Confirm" control 324, the first flushing parameters take effect, and the first flushing parameters can be adopted. When the user sets the first flushing parameters by the "Confirm" control 324, the first flushing parameters take effect, and flushing can be performed using the first flushing parameters.

In this regard, when adjusting the flushing parameters, the adjustment values should be within a permissible range so as to avoid adverse consequences caused by misadjustment. Thus, in some examples, after receiving the second flushing parameter input by the user in the flushing parameter adjustment interface, the system determines whether the second flushing parameter input by the user exceeds the preset threshold value, and, if it does, a prompt message is output, so as to indicate to the user that the parameter adjustment is out of range. The user may then correctly adjust the flushing parameter, thereby ensuring the accuracy of the flushing parameter. The prompting information may be a voice alarm, an alarm light blinking, a text prompt, an icon prompt, a highlight prompt, a pop-up window prompt, etc.

S203, according to the first flushing parameter, the nutrient infusion apparatus is controlled to flush.

As an example, when the control device of the nutrient infusion apparatus of the invention determines the flushing parameter, the determined flushing parameters are used to control the nutrient infusion apparatus for flushing at the moment when flushing needs to be performed. For example, intermittent feeding may require flushing before and after each feeding separately, and continuous feeding may require flushing during feeding, which may be determined according to the specific feeding situation.

Embodiments of the invention provide a method for controlling a nutrient infusion apparatus, including: acquiring a feeding parameter; automatically determining a first flushing parameter according to the feeding parameter and a preset flushing rule; and controlling the nutrient infusion apparatus to flush according to the first flushing parameter. Using the method of the invention, healthcare personnel, when performing parameter setting, only need to set the feeding parameter, and the corresponding flushing parameter can be determined automatically, without having to set the flushing parameter manually, thereby improving the efficiency of parameter setting. Furthermore, relative to manually setting the flushing parameter, the accuracy of automatically determining the flushing parameter according to the feeding parameter is also higher, which improves the accuracy of parameter setting, thereby improving the accuracy of the flushing control.

Figure 4:
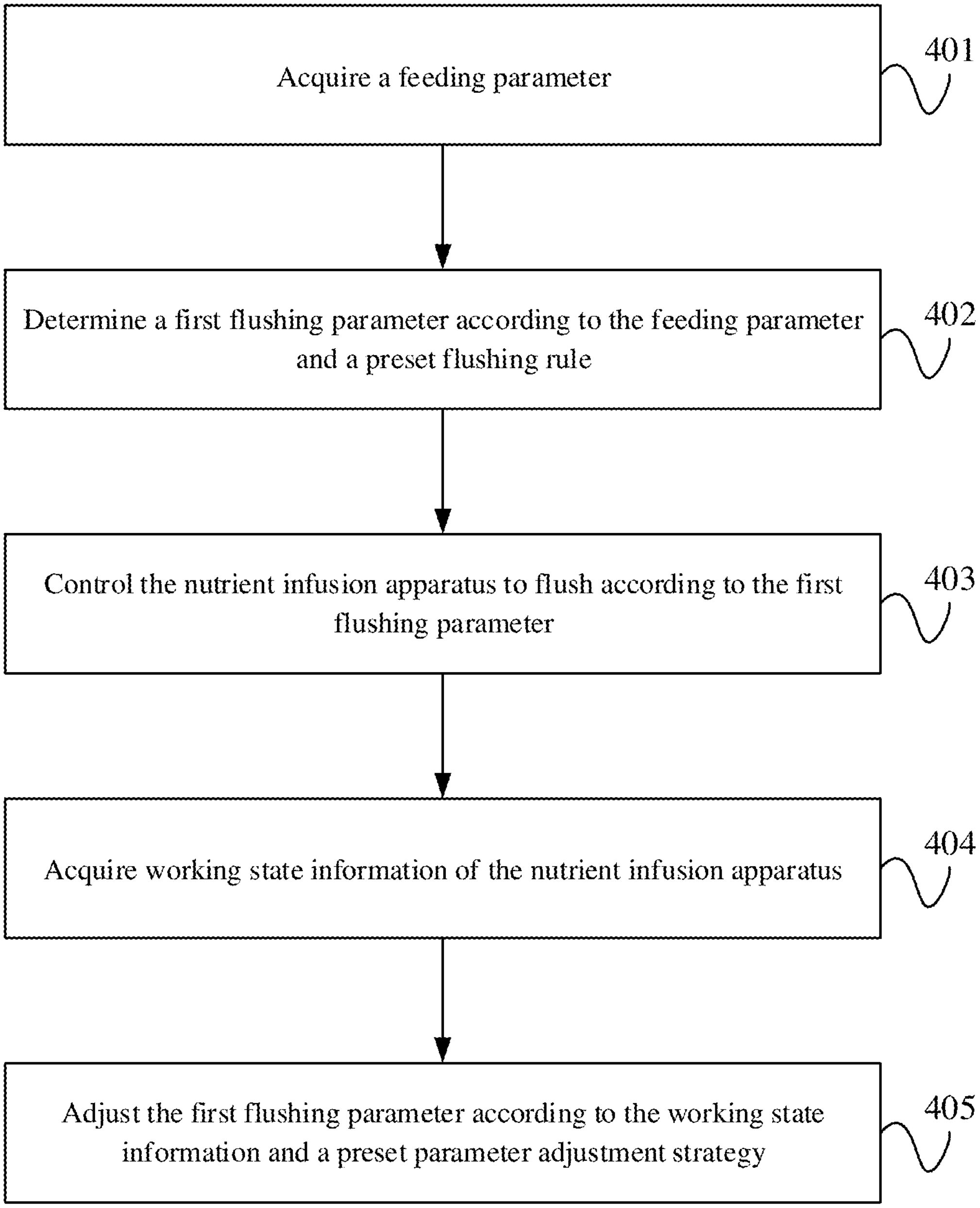
FIG. 4 shows a flowchart of another method for controlling the nutrient infusion apparatus according to an embodiment of the invention.

FIG. 4 shows a flowchart of another method for controlling the nutrient infusion apparatus according to an embodiment of the invention. As shown in FIG. 4, the method for controlling the nutrient infusion apparatus provided by the embodiment includes the following steps.

S401, feeding parameters are acquired.

S402, a first flushing parameter is determined according to the feeding parameters and a preset flushing rule.

S403, the nutrient infusion apparatus is controlled to flush according to the first flushing parameter.

As an example, the specific realization of steps S401 to S403 is similar to step S201 to step S203, and will not be repeated herein.

S404: working state information of the nutrient infusion apparatus is acquired.

As an example, after setting the feeding parameters and the flushing parameters, the control device of the nutrient infusion apparatus of the invention may continue to control the nutrient infusion apparatus to carry out nutrient solution feeding. During the actual feeding process, the working state of the nutrient infusion apparatus will change, and there will be some difference between the actual feeding parameters and the set target feeding parameters. In order to more accurately adjust the flushing parameters, during the feeding process, the control device can also obtain the practical working state information of the nutrient infusion apparatus, so that it can subsequently adjust the flushing parameters to achieve a better flushing effect.

The working state information may include at least one of the following: feeding pause duration, manual flushing information, and tube blockage information. The tube blockage information includes a tube blockage frequency and/or a tube blockage pressure value.

As an example, the feeding pause duration refers to the a duration experienced by the healthcare personnel while manually controlling the feeding pause and then manually starting the feeding according to the actual feeding situation. Manual flushing information is the information that the healthcare personnel manually controls to cause the nutrient infusion apparatus to flush according to the actual feeding situation. Tube blockage refers to when the nutrient solution cannot be infused according to normal conditions due to the existence of blockage in the delivery tubing; the degree of blockage may be determined by the tube blockage frequency and/or the tube blockage pressure value.

As an example, during the actual feeding process, depending on the therapeutic needs, the healthcare personnel may suspend the feeding or perform operations such as manual flushing. When the nutrient solution stays in the tube for more than a certain duration, it may cause tube blockage, and when the tube is blocked or is about to be blocked, the tube blockage pressure value and/or the tube blockage frequency will also change. When the tube blockage pressure value and/or tube blockage frequency reaches a preset threshold, it is necessary to adjust the subsequent flushing parameters in order to avoid serious blockage that may affect the feeding effect. After manual flushing, if the original flushing parameters are still used for flushing, it is possible for this to cause excessive flushing, resulting in diarrhea and other complications. It is then also necessary to adjust the subsequent flushing parameters to avoid excessive flushing. That is, when the working state information of the nutrient infusion apparatus changes, the corresponding flushing parameters should also be adjusted to be more applicable to the actual feeding situation.

S405: According to the working state information and the preset parameter adjustment strategy, the first flushing parameter is adjusted.

As an example, the control device of the nutrient infusion apparatus of the invention may adjust the subsequent flushing parameters according to the obtained working state information of the nutrient infusion apparatus and the preset parameter adjustment strategy, so as to obtain a more effective flushing.

As an example, the step of adjusting the first flushing parameter according to the working state information and the preset parameter adjustment strategy may include: adjusting the first flushing parameter according to the working state information when it is determined that the working state information satisfies the preset parameter adjustment condition.

As an example, when the acquired working state information is a feeding pause duration, the step of adjusting the first flushing parameter according to the working state information and the preset parameter adjustment strategy may be as follows: determining whether the feeding pause duration exceeds a preset value, and if it is determined that the feeding pause duration exceeds the preset value, an indication is generated that there may be a risk of blockage in the tube. In this circumstance, flushing may be controlled so as to take place immediately prior to the start of feeding by the nutrient infusion apparatus, and subsequent flushing parameters are adjusted, such as reducing the next flushing volume and flushing duration, extending the next flushing time, or the like, in order to avoid excessive flushing in a short period of time.

As an example, when the acquired working state information is manual flushing information, i.e., when it is determined that there is a situation in which the healthcare personnel should manually control the nutrient infusion apparatus to flush manually, in order to avoid excessive flushing within a short period of time. The step of adjusting the first flushing parameter according to the working state information and the preset parameter adjustment strategy may then be as follows: adjusting the subsequent flushing parameter, such as canceling the last flushing, extending the next flushing time, or, reducing the next flushing volume and flushing duration, so as to avoid excessive flushing within a short period of time.

As an example, when the acquired working state information is the tube blockage information, the step of adjusting the first flushing parameter according to the working state information and the preset parameter adjustment strategy may be as follows: according to the tube blockage information, the degree of tube blockage is determined, and the flushing parameters are adjusted according to the degree of tube blockage. For example, if it is determined that a tube blockage or a blockage warning has occurred or is about to occur according to the tube blockage frequency and/or the tube blockage pressure value, the nutrient infusion apparatus may be controlled to automatically start flushing to timely unblock the tube to prevent blockage. In addition, the flushing time may be appropriately shortened and the flushing volume increased according to a specific value of the tube blockage frequency and/or a specific value of the tube blockage pressure, so as to minimize the occurrence of the blockage. For example, when the tube blockage frequency and/or the tube blockage pressure value is large, the flushing time may be shortened and the flushing volume increased, so as to reduce the occurrence of blocking.

As an example, when it is determined that the work state information satisfies the preset parameter adjustment conditions, the first flushing parameters may be adjusted according to the specific value of the work state information, and the nutrient infusion apparatus may be controlled to flush with the adjusted flushing parameter, so as to reduce the risk of tube blockage, and also to avoid excessive flushing within a short period of time, thereby improving the accuracy of the flushing control, and also improving the therapeutic effect.

In one possible example, after adjusting the first flushing parameters according to the work state information and the preset parameter adjustment strategy, in order to make it easier for the healthcare professional to view the parameter adjustment record, conduct the infusion review, and more accurately understand the flushing situation during the infusion process, the method of the invention may also include the following step:

Details of the parameter adjustment during the infusion process are recorded. The parameter adjustment details include at least one the following: a flushing parameter adjustment reason, a flushing parameter adjustment time, values before and after the flushing parameter adjustment.

As an example, with the recorded parameter adjustment details, the healthcare personnel can more accurately understand the flushing situation during the infusion process, so as to subsequently set up a more accurate flushing regimen, in order to provide better therapeutic services to the feeding subject.

The method for controlling a nutrient infusion apparatus provided by the embodiment of the invention includes: acquiring feeding parameters, automatically determining a first flushing parameter according to the feeding parameters and a preset flushing rule, controlling the nutrient infusion apparatus to flush according to the first flushing parameter, acquiring working state information of the nutrient infusion apparatus, and adjusting the first flushing parameter according to the working state information and the preset parameter adjustment strategy. Accordingly, after the user sets the feeding parameters, the invention can directly and automatically determine the flushing parameters according to the preset flushing rules, without the need for the healthcare personnel to manually set the flushing parameters again, which improves the efficiency of parameter setting. Furthermore, the invention may adjust the flushing parameters according to the actual feeding situation during the actual feeding process, thereby reducing the risk of tube blockage, and avoiding excessive flushing within a short period of time, thereby improving the flushing control accuracy, and also improving the therapeutic effect.

Figure 5:
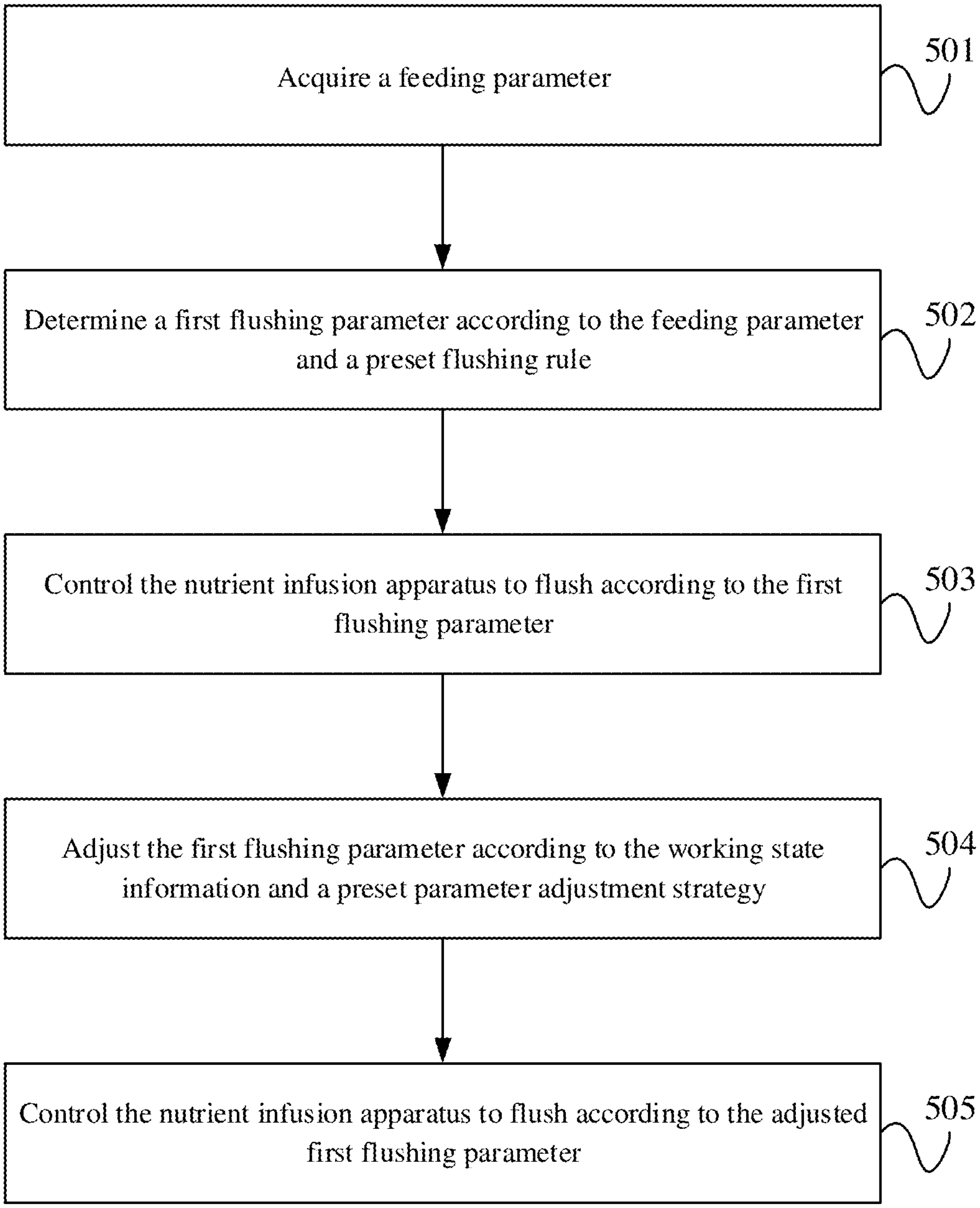
FIG. 5 shows a flowchart of yet another method for controlling the nutrient infusion apparatus according to an embodiment of the invention.

FIG. 5 shows a flowchart of yet another method for controlling the nutrient infusion apparatus according to an embodiment of the invention. As shown in FIG. 5, the method for controlling the nutrient infusion apparatus provided by the embodiment includes the following steps.

S501, feeding parameters are acquired.

S502, a first flushing parameter is determined according to the feeding parameter and a preset flushing rule.

S503, working state information of the nutrient infusion apparatus is acquired.

S504, the first flushing parameters are adjusted according to the working state information and the preset parameter adjustment strategy.

S505: the nutrient infusion apparatus is controlled to flush according to the adjusted first flushing parameters.

As an example, the specific realization of steps S501-S502 is similar to steps S201-S202, the specific realization of steps S50-S504 is similar to steps S404-S405, and the specific realization of step S505 is similar to step S203, and will not be repeated herein.

The method for controlling a nutrient infusion apparatus provided by the embodiment of the invention includes: acquiring feeding parameters, automatically determining a first flushing parameter according to the feeding parameters and a preset flushing rule, controlling the nutrient infusion apparatus to flush according to the first flushing parameter, acquiring working state information of the nutrient infusion apparatus, and adjusting the first flushing parameter according to the working state information and the preset parameter adjustment strategy. Accordingly, after the user sets the feeding parameters, the invention can directly and automatically determine the flushing parameters according to the preset flushing rules, without the need for the healthcare personnel to manually set the flushing parameters again, which improves the efficiency of parameter setting. Furthermore, in this embodiment, the working state information of the nutrient infusion apparatus is acquired before flushing according to the first flushing parameters, and the first flushing parameters are adjusted according to the working state information and the preset parameter adjustment strategy, so as to control the nutrient infusion apparatus to flush according to the adjusted first flushing parameters, which not only improves the accuracy of the flushing parameters, but also conforms to the actual situation needs, and achieve a better flushing effect during flushing.

The following is an embodiment of the device embodiment of the invention, which can be used to perform the methods in embodiments of the invention. For details not disclosed here for the device embodiments of the invention, please refer to the method embodiments of the invention described above.

Figure 6:
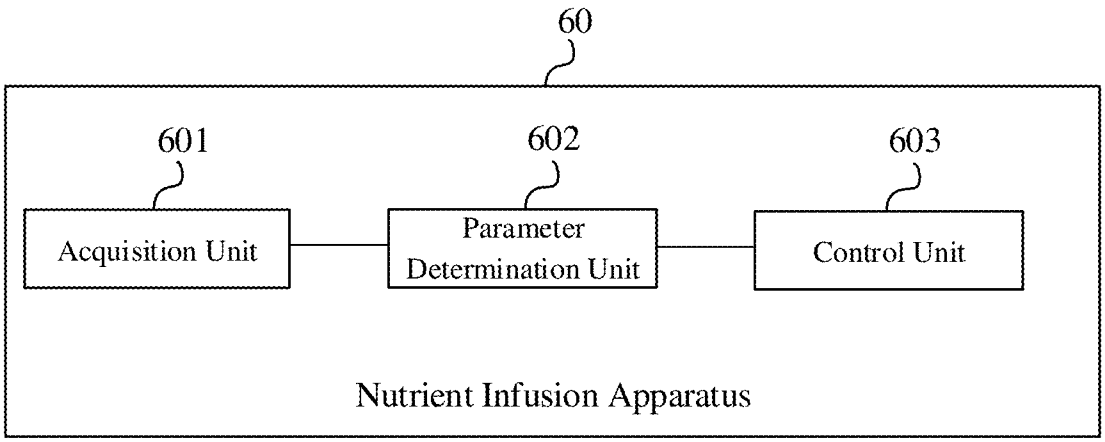
FIG. 6 is a schematic structural diagram of a nutrient infusion apparatus according to an embodiment of the invention.

FIG. 6 shows a schematic structural diagram of a nutrient infusion apparatus according to an embodiment of the invention. As shown in FIG. 6, the nutrient infusion apparatus 60 according to the embodiment of the invention includes an acquisition unit 601, a parameter determination unit 602, and a control unit 603.

The acquisition unit 601 is configured to acquire feeding parameters.

The parameter determination unit 602 is configured to determine a first flushing parameter according to the feeding parameter and a preset flushing rule.

The control unit 603 is configured to control the nutrient infusion apparatus to flush according to the first flushing parameter.

The apparatus provided in this embodiment can be used to perform the method of the above embodiments, the realization principle and technical effect of which are similar and will not be repeated herein.

Figure 7:
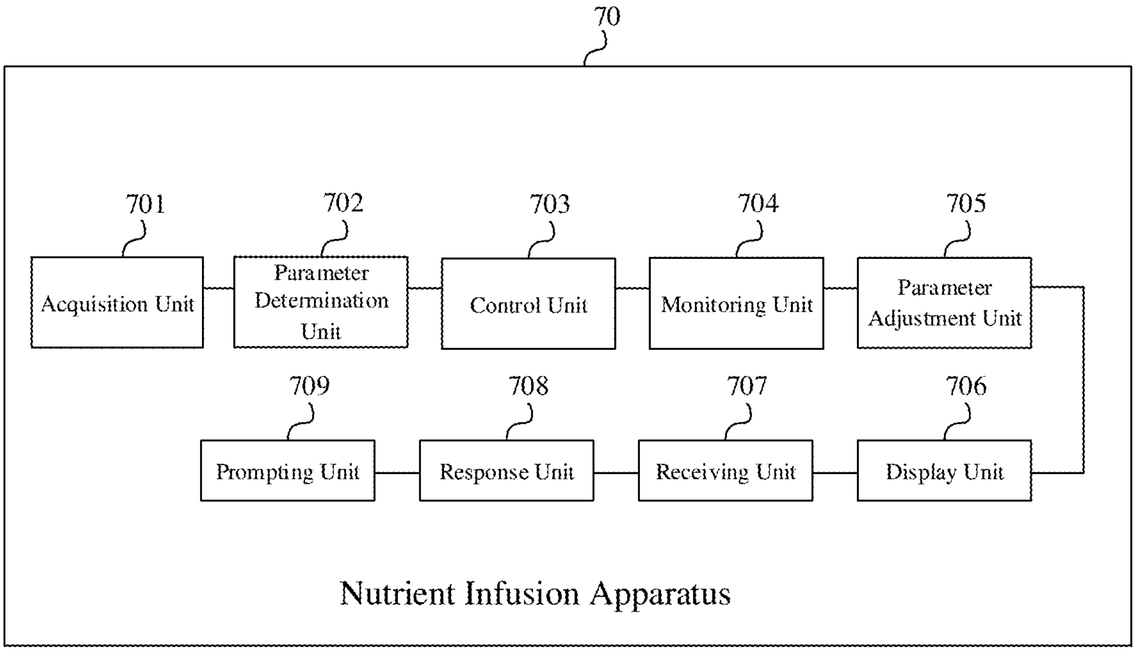
FIG. 7 is a schematic structural diagram of another nutrient infusion apparatus according to an embodiment of the invention.

FIG. 7 is a schematic structural diagram of another nutrient infusion apparatus according to an embodiment of the invention. As shown in FIG. 7, the nutrient infusion apparatus 70 according to the embodiment of the invention includes an acquisition unit 701, a parameter determination unit 702, and a control unit 703.

The acquisition unit 701 is configured to acquire feeding parameters.

The parameter determination unit 702 is configured to determine a first flushing parameter according to the feeding parameter and a preset flushing rule.

The control unit 703 is configured to control the nutrient infusion apparatus to flush according to the first flushing parameter.

In one example, the feeding parameters include at least one of the following: a nutrient solution type, a nutrient solution concentration, a nutrient solution feeding volume, a feeding mode, a feeding rate, a feeding time, and a patient type.

In one example, the first flushing parameter includes at least one of the following: a flushing mode, a flushing rate, a total flushing volume, a flushing time, a flushing volume per cycle, and a number of flushing cycles.

In one example, the nutrient infusion apparatus 70 further includes a monitoring unit 6704 and a parameter adjustment unit 705.

The monitoring unit 704 is configured to obtain working state information of the nutrient infusion apparatus.

The parameter adjustment unit 705 is configured to adjust the first flushing parameter according to the working state information and a preset parameter adjustment strategy.

In one example, the working state information includes at least one of the following: a feeding pause duration, manual flushing information, and tube blockage information. The tube blockage information includes a tube blockage frequency and/or a tube blockage pressure value.

In one example, the parameter adjustment unit 705 is configured to adjust the first flushing parameter according to the working state information when it is determined that the working state information satisfies a preset parameter adjustment condition.

In one example, the nutrient infusion apparatus 70 further includes a display unit 706, a receiving unit 707, and a response unit 708.

The display unit 706 is configured to display a flushing parameter adjustment interface.

The receiving unit 707 is configured to receive an input from a user in the flushing parameter adjustment interface to determine a second flushing parameter input by the user.

The response unit 708 is configured to adjust the first flushing parameter according to the second flushing parameter entered by the user.

In one example, the nutrient infusion apparatus 70 further includes a prompting unit 709.

The prompting unit 709 is configured to output a prompt message when it is determined that the second flushing parameter input by the user exceeds a preset threshold.

The apparatus in this embodiment can be used to perform the methods of the above embodiments, the realization principles and technical effects of which are similar and will not be repeated herein.

It is to be noted that it should be understood that the division of the various modules of the above device is merely a logical functional division, and may be fully or partially integrated into a physical entity or physically separated when actually realized. These modules may all be realized in the form of software invoked through processing elements; may also be realized in the form of hardware; may also be part of the module through the processing elements invoked in the form of software, part of the module through the form of hardware. In addition, it may also be stored in the form of program code in the memory of the above device, which is called by one of the processing elements of the above device and performs the functions of the above data processing module. Other modules are realized similarly. In addition all or some of these modules may be integrated together or may be realized independently. The processing element here may be an integrated circuit with signal processing capability. In the realization, the steps of the above method or each of the above modules may be accomplished by integrated logic circuits of hardware in the processor element or by instructions in the form of software.

Figure 8:
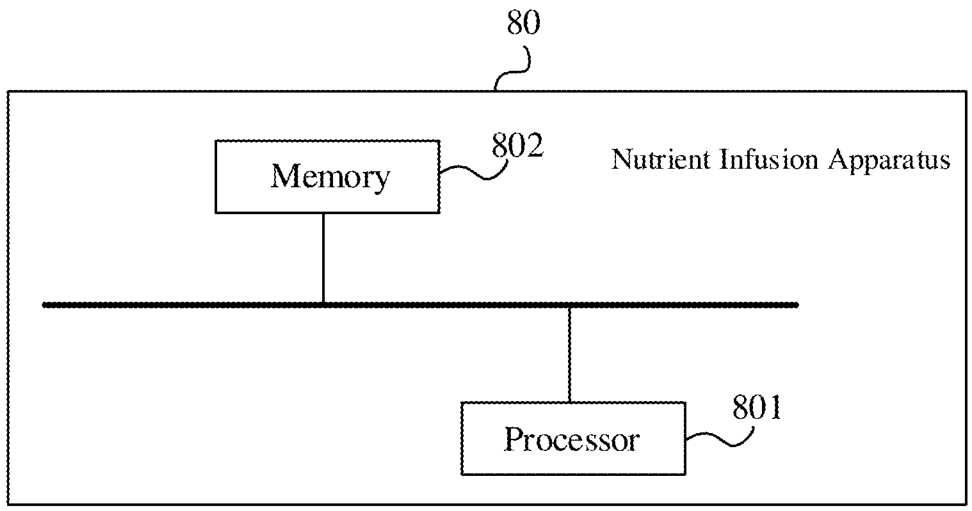
FIG. 8 is a schematic structural diagram of yet another nutrient infusion apparatus according to an embodiment of the invention.

FIG. 8 is a schematic structural diagram of yet another nutrient infusion apparatus according to an embodiment of the invention. As shown in FIG. 8, the nutrient infusion apparatus 80, includes: a processor 801, and a memory 802 in communication with the processor.

The memory 802 is configured to store computer-executable instructions, and the processor 801 is configured execute the computer-executable instructions stored in the memory 802 to implement a method as any of the foregoing.

In specific implementations of the above-described apparatus, it should be understood that the processor may be a Central Processing Unit (CPU), and may also be other general-purpose processors, a Digital Signal Processor (DSP), an Application Specific Integrated Circuit (ASIC) and so on. The general purpose processor may be a microprocessor or the processor may be any conventional processor. The method disclosed in conjunction with embodiments of the invention may be directly performed in a hardware processor, or performed with a combination of hardware and software modules in the processor.

Embodiments of the invention also provide a computer-readable storage medium having computer-executable instructions stored therein. The computer-executable instructions are configured to implement the method as in any of the preceding claims when executed by the processor.

It will be appreciated by one of ordinary skill in the art that all or some of the steps for realizing each of the foregoing embodiments of the method may be accomplished by hardware associated with computer instructions. The foregoing program may be stored in a computer-readable storage medium. The program, when executed, performs the steps including each of the above-described method embodiments. The foregoing storage medium includes a ROM, a RAM, a magnetic disk, or a CD-ROM, and various other media that can store program code.

Embodiments of the invention also provide a computer program product including a computer program which, when executed by a processor, is configured to implement a method as in any of the foregoing.

Other embodiments of the invention will readily come to mind to those skilled in the art upon consideration of the specification and practice of the invention disclosed herein. The invention is intended to cover any variations, uses, or adaptations of the invention which follow the general principles of the invention and include common knowledge or customary technical means in the art not disclosed herein. The specification and embodiments are to be regarded as examples only, and the true scope and spirit of the invention is indicated by the following claims.

It is to be understood that the invention is not limited to the precise structure which has been described above and illustrated in the accompanying drawings, and that various modifications and changes may be made without departing from its scope. The scope of the invention is limited only by the appended claims.

The invention claimed is:

1. A method for controlling a nutrient infusion apparatus, comprising:

acquiring at least one feeding parameter;

automatically determining a set of flushing parameters according to the at least one feeding parameter and a preset flushing rule;

automatically determining a first flushing parameter from the set of flushing parameters according to the at least one feeding parameter and the preset flushing rule, automatically adjusting said flushing rule depending on the at least one feeding parameter;

and controlling the nutrient infusion apparatus to flush a feeding tube according to the first flushing parameter.

2. The method of claim 1, wherein the at least one feeding parameter comprises at least one of the following: a nutrient solution type, a nutrient solution concentration, a nutrient solution feeding volume, a feeding mode, a feeding rate, a feeding time, and a patient type.

3. The method of claim 1, wherein the first flushing parameter comprises at least one of the following: a flushing mode, a flushing rate, a total flushing volume, a flushing time, a flushing volume per cycle, and a number of flushing cycles.

4. The method of claim 1, wherein, after the step of determining the first flushing parameter according to the at least one feeding parameter and preset flushing rule, the method further comprises:

acquiring working state information of the nutrient infusion apparatus; and adjusting the first flushing parameter according to the working state information and a preset parameter adjustment strategy that includes adjustment over positive flushing volumes.

5. The method of claim 4, wherein the working state information comprises at least one of the following: feeding pause duration, manual flushing information, and tube blockage information; wherein the tube blockage information comprises at least one of a tube blockage frequency and a tube blockage pressure value.

6. The method of claim 4, wherein the step of adjusting the first flushing parameter according to the working state information and the preset parameter adjustment strategy comprises:

adjusting the first flushing parameter according to the working state information when it is determined that the working state information satisfies a preset parameter adjustment condition.

7. The method of claim 4, further comprising:

determining a degree of blockage of the feeding tube by sensing at least one of a feeding tube blockage frequency and a feeding tube blockage pressure value;

detecting one of actual and impending blockage of the feeding tube by evaluating the degree of blockage; and automatically initiating a flushing cycle of the feeding tube upon detecting the one of actual and impending blockage.

8. The method of claim 1, further comprising:

displaying a flushing parameter adjustment interface;

receiving input from a user in the flushing parameter adjustment interface and determining a second flushing parameter input by the user; and adjusting the first flushing parameter according to the second flushing parameter entered by the user.

9. The method of claim 8, further comprises:

outputting a prompt message when it is determined that the second flushing parameter input by the user exceeds a preset threshold.

10. A nutrient infusion apparatus, comprising:

an acquisition unit configured to acquire at least one feeding parameter;

a parameter determination unit configured to automatically determine a set of flushing parameters according to the at least one feeding parameter and a preset flushing rule, to determine a first flushing parameter from among the set of flushing parameters according to the at least one feeding parameter and the preset flushing rule, and to automatically adjust said flushing rule depending on the at least one feeding parameter; and a control unit configured to automatically control the nutrient infusion apparatus to flush according to the first flushing parameter.

11. A method for controlling a nutrient infusion apparatus, comprising:

acquiring a feeding parameter;

automatically determining a first flushing parameter according to the feeding parameter and a preset flushing rule; and controlling the nutrient infusion apparatus to flush a feeding tube according to the first flushing parameter;

after determining the first flushing parameter according to the feeding parameter and preset flushing rule, acquiring working state information of the nutrient infusion apparatus and adjusting the first flushing parameter according to the working state information and a preset parameter adjustment strategy;

determining a degree of blockage of the feeding tube by sensing at least one of a feeding tube blockage frequency and a feeding tube blockage pressure value;

detecting one of actual and impending blockage of the feeding tube by evaluating the degree of blockage; and automatically initiating a flushing cycle of the feeding tube upon detecting the one of actual and impending blockage.

* * * * *